(12) United States Patent
Bray

(10) Patent No.: US 6,984,234 B2
(45) Date of Patent: Jan. 10, 2006

(54) BONE PLATE STABILIZATION SYSTEM AND METHOD FOR ITS USE

(75) Inventor: Robert S. Bray, Studio City, CA (US)

(73) Assignee: RSB Spine LLC, Cleveland, OH (US)

( * ) Notice: Subject to any disclaimer, the term of this patent is extended or adjusted under 35 U.S.C. 154(b) by 337 days.

(21) Appl. No.: 10/419,652

(22) Filed: Apr. 21, 2003

(65) Prior Publication Data

US 2004/0210219 A1    Oct. 21, 2004

(51) Int. Cl.
*A61B 17/80* (2006.01)

(52) U.S. Cl. .......................... 606/69; 606/61

(58) Field of Classification Search ............. 606/61, 606/69, 70, 71; 623/17.16
See application file for complete search history.

(56) References Cited

U.S. PATENT DOCUMENTS

| | | |
|---|---|---|
| 4,599,086 A | 7/1986 | Doty |
| 4,955,908 A | 9/1990 | Frey et al. |
| 5,425,773 A | 6/1995 | Boyd et al. |
| 5,645,599 A | 7/1997 | Samani |
| 5,800,433 A * | 9/1998 | Benzel et al. .......... 606/61 |
| 5,865,846 A | 2/1999 | Bryan et al. |
| 5,888,223 A | 3/1999 | Bray, Jr. |
| 6,066,175 A | 5/2000 | Henderson et al. |
| 6,228,085 B1 | 5/2001 | Theken et al. |
| 6,342,074 B1 | 1/2002 | Simpson |
| 6,645,208 B2 | 11/2003 | Apfelbaum et al. |
| 2002/0147450 A1 * | 10/2002 | LeHuec et al. .......... 606/61 |
| 2003/0028250 A1 | 2/2003 | Reiley et al. |
| 2003/0120274 A1 | 6/2003 | Morris et al. |
| 2003/0130661 A1 | 7/2003 | Osman |

FOREIGN PATENT DOCUMENTS

EP        0 179 695       4/1986

* cited by examiner

*Primary Examiner*—David O. Reip
(74) *Attorney, Agent, or Firm*—Pearne & Gordon LLP (57) ABSTRACT

A method for joining first and second bones is provided. The method comprises inserting between the side surfaces of the bones a base plate having a first end nearer the first bone and a second end nearer the second bone. The base plate has a first screw hole extending through the first end and a second screw hole extending through the second end. A first bone screw is introduced through the first screw hole and into the first bone. The first bone screw is introduced at an angle relative to the top surface of the bone ranging from about 20° to about 60°. A second bone screw is introduced through the second screw hole and into the second bone. The second bone screw is introduced at an angle relative to the top surface of the bone ranging from about 20° to about 70°. At least a part of the first bone screw and at least a part of the second bone screw are covered to prevent the first and second bone screws from backing out of the first and second bones, respectively.

41 Claims, 6 Drawing Sheets

BONE PLATE STABILIZATION SYSTEM AND METHOD FOR ITS USE

FIELD OF THE INVENTION

The present invention is directed to a bone plate system that is particularly useful for assisting with the surgical arthrodesis (fusion) of two bones together, and more particularly, to a bone plate that provides and controls limited movement between the bones during fusion.

BACKGROUND

The spinal column of vertebrates provides support to bear weight and protection to the delicate spinal cord and spinal nerves. The spinal column comprises a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior which covers the neural structures. Between each vertebral body is an intervertebral disk, a cartilaginous cushion to help absorb impact and dampen compressive forces on the spine. To the posterior the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition congenital or acquired deformities can cause abnormal angulation or slippage of the spine. Slippage (spondylolisthesis) anterior of one vertebral body on another can cause compression of the spinal cord or nerves. Patients who suffer from one of more of these conditions often experience extreme and debilitating pain, and can sustain permanent neurologic damage if the conditions are not treated appropriately.

One technique of treating these disorders is known as surgical arthrodisis of the spine. This can be accomplished by removing the intervertebral disk and replacing it with bone and immobilizing the spine to allow the eventual fusion or growth of the bone across the disk space to connect the adjoining vertebral bodies together. The stabilization of the vertebra to allow fusion is often assisted by a surgically implanted device to hold the vertebral bodies in proper alignment and allow the bone to heal, much like placing a cast on a fractured bone. Such techniques have been effectively used to treat the above described conditions and in most cases are effective at reducing the patient's pain and preventing neurologic loss of function. However, there are disadvantages to the present stabilization devices.

The spinal fixation device needs to allow partial sharing of the weight of the vertebral bodies across the bone graft site. Bone will not heal if it is stress shielded from all weight bearing. The fixation device needs to allow for this weight sharing along with the micromotion that happens during weight sharing until the fusion is complete, often for a period of three to six months or longer, without breakage. The device must be strong enough to resist collapsing forces or abnormal angulation during the healing of the bone. Loss of alignment during the healing phase can cause a poor outcome for the patient. The device must be secure in its attachment to the spine to prevent migration of the implant or backout of the screws from the bone which could result in damage to the structures surrounding the spine, resulting in severe and potentially life threatening complications. The device must be safely and consistently implanted without damage to the patient.

Several types of anterior spinal fixation devises are in use currently. One technique involves placement of screws all the way through the vertebral body, called bicortical purchase. The screws are placed through a titanium plate but are not attached to the plate. This device is difficult to place, and overpenetration of the screws can result in damage to the spinal cord. The screws can back out of the plate into the surrounding tissues as they do not fix to the plate. Several newer generation devices have used a unicortical purchase of the bone, and in some fashion locking the screw to the plate to provide stability and secure the screw from backout. Problems have resulted from over ridged fixation and stress shielding, resulting in nonunion of the bony fusion, chronic micromotion during healing resulting in stress fracture of the fixation device at either the screw or the plate, insecure locking of the screw to the plate resulting in screw backout, or inadequate fixation strength and resultant collapse of the graft and angulation of the spine.

These devices are often designed to support and bridge across a group of vertebrae, for example a group of three. Because these devices are typically bridged across the bone, for example in the cervical region, they occasionally aggravate the esophagus, making it difficult for one to swallow food. In addition, the screws are installed into the bone normal, i.e., 90° to the plate's surface. Local angularity in the vertebral column often causes high shearing stresses to be applied to the screws. These stresses may fatigue the screws or cause deformation of the screw holes.

Thus, there is a need for a device and method of supporting adjacent vertebrae that avoids these problems and risks to the patient.

SUMMARY OF THE INVENTION

The present invention is directed to a bone stabilization device and a method for its use. In one embodiment, the invention is directed to a method for joining first and second bones having top surfaces and side surfaces generally facing each other. The method comprises inserting between the side surfaces of the bones a base plate having a first end nearer the first bone and a second end nearer the second bone. The base plate has a first screw hole extending through the first end and a second screw hole extending through the second end. A first bone screw is introduced through the first screw hole and into the first bone, wherein the first bone screw is introduced at an angle relative to the top surface of the bone ranging from about 20° to about 60°. A second bone screw is introduced through the second screw hole and into the second bone, wherein the second bone screw is introduced at an angle relative to the top surface of the bone ranging from about 20° to about 70°. At least a part of the first bone screw and at least a part of the second bone screw are covered to prevent the first and second bone screws from backing out of the first and second bones, respectively.

In another embodiment, the invention is directed to bone stabilization plate system comprising a base plate having bottom surface and first and second ends. The first end comprises a first bone screw region having a first bone screw hole extending therethrough at an angle relative to the bottom surface of the base plate ranging from about 20° to about 60°. The second end comprises a second bone screw region having a second bone screw hole extending therethrough at an angle relative to the bottom surface of the base plate ranging from about 20° to about 70°. The system further includes a first bone screw capable of securing the base plate to a first bone by insertion through the first bone screw hole, and a second bone screw capable of securing the base plate to a second bone by insertion through the second bone screw hole. A bone screw retaining means is provided for securedly covering at least a part of the first and second bone screws to prevent the bone screws from backing out from the first and second bones.

In yet another embodiment, the invention is directed to a method for joining vertebral bodies. The method comprises inserting between side surfaces of first and second adjacent vertebral body a first base plate having a first end nearer the first vertebral body and a second end nearer the second vertebral body. The first base plate has a first screw hole extending through the first end and a second screw hole extending through the second end. A first bone screw is introduced through the first screw hole and into the first bone, and a second bone screw is introduced through the second screw hole and into the second bone. At least a part of the first bone screw and at least a part of the second bone screw are covered to prevent the first and second bone screws from backing out of the first and second bones, respectively. A second base plate having a first end nearer the second vertebral body and a second end nearer a third vertebral body that is adjacent the second vertebral body is inserted between a side surface of the second vertebral body and a side surface of the third vertebral body. A third bone screw is introduced through the first screw hole of the second base plate and into the second bone and a fourth bone screw is inserted through the second screw hole of the second base plate and into the third bone. At least a part of the third bone screw and at least a part of the fourth bone screw are covered to prevent the third and fourth bone screws from backing out of the second and third bones, respectively. The first base plate does not contact the second base plate.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION

The present invention is directed to a bone stabilization plate system for stabilizing two adjacent bones (including bone fragments), such as adjacent vertebral bodies, while they heal, as well as to methods for its use. A particularly preferred bone stabilization plate system 10 constructed in accordance with the present invention is shown in FIGS. 1 to 4. The depicted bone stabilization plate system comprises a base plate 20 having first and second ends, and including a primary member 21 and a secondary member 22 at the second end of the base plate. The secondary member 22 is angled relative to the primary member 21, as discussed further below, although other designs are contemplated within the scope of the invention.

The base plate 20 may be made of any suitable material, and is preferably made from titanium or a titanium alloy. The thickness of the base plate 20 is not critical, and preferably ranges from about 1 mm to about 2 mm, and more preferably is about 1.6 mm. The thickness of the base plate 20 will depend on the particular application.

Figure 1:
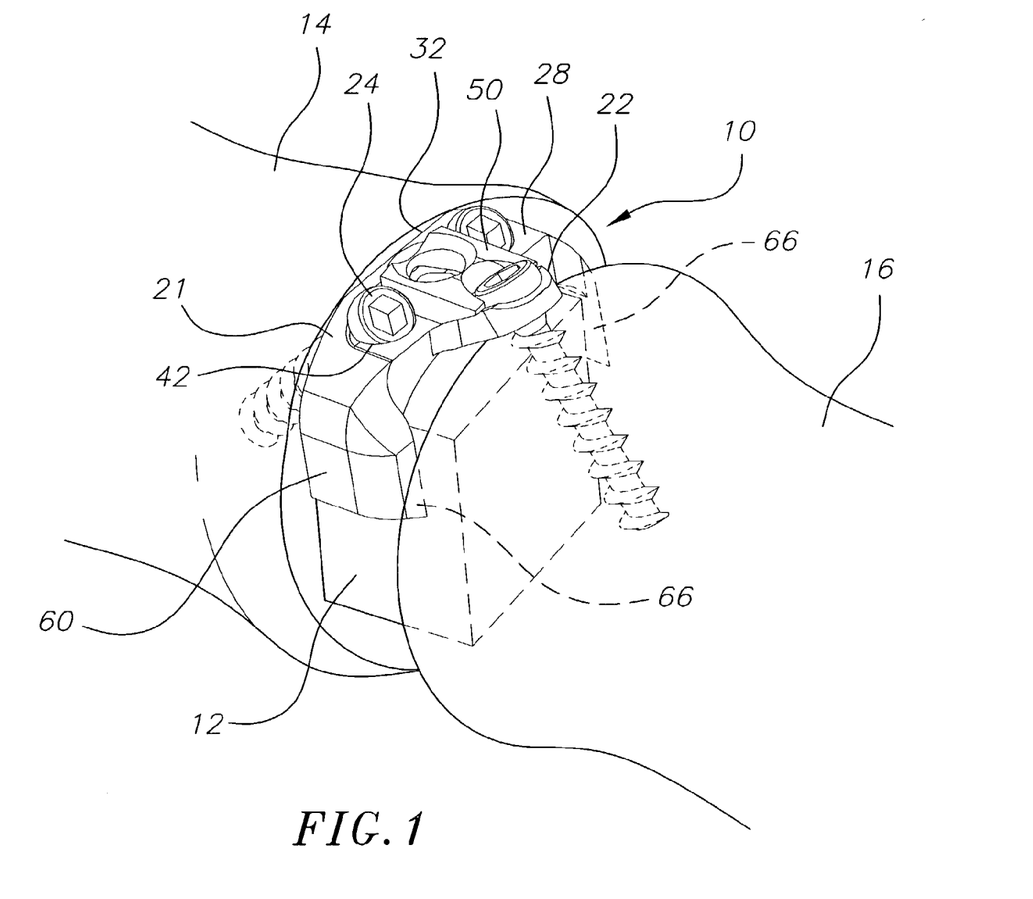
FIG. 1 is a perspective view of a bone stabilization plate system according to the invention that is assembled between adjacent vertebrae.
Figure 2:
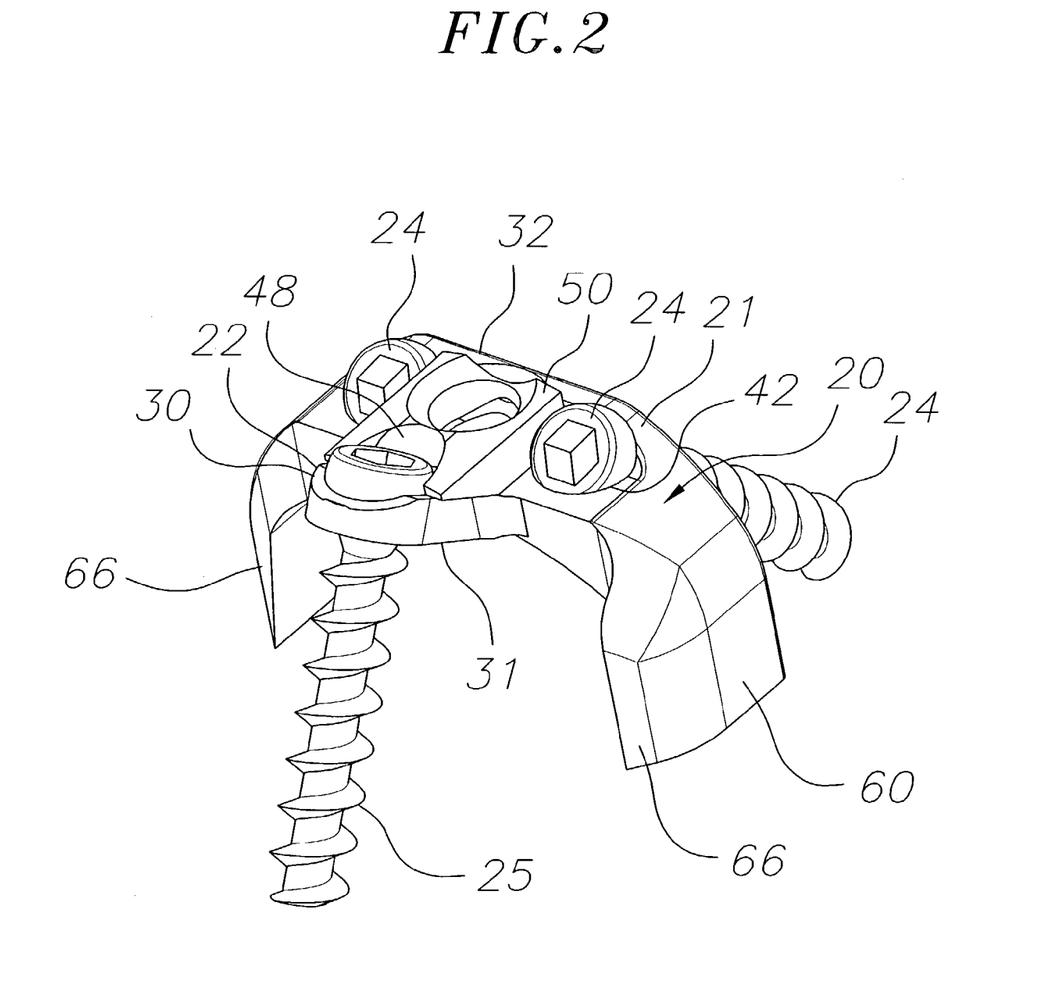
FIG. 2 is a perspective view of the bone stabilization plate system of FIG. 1.
Figure 3:
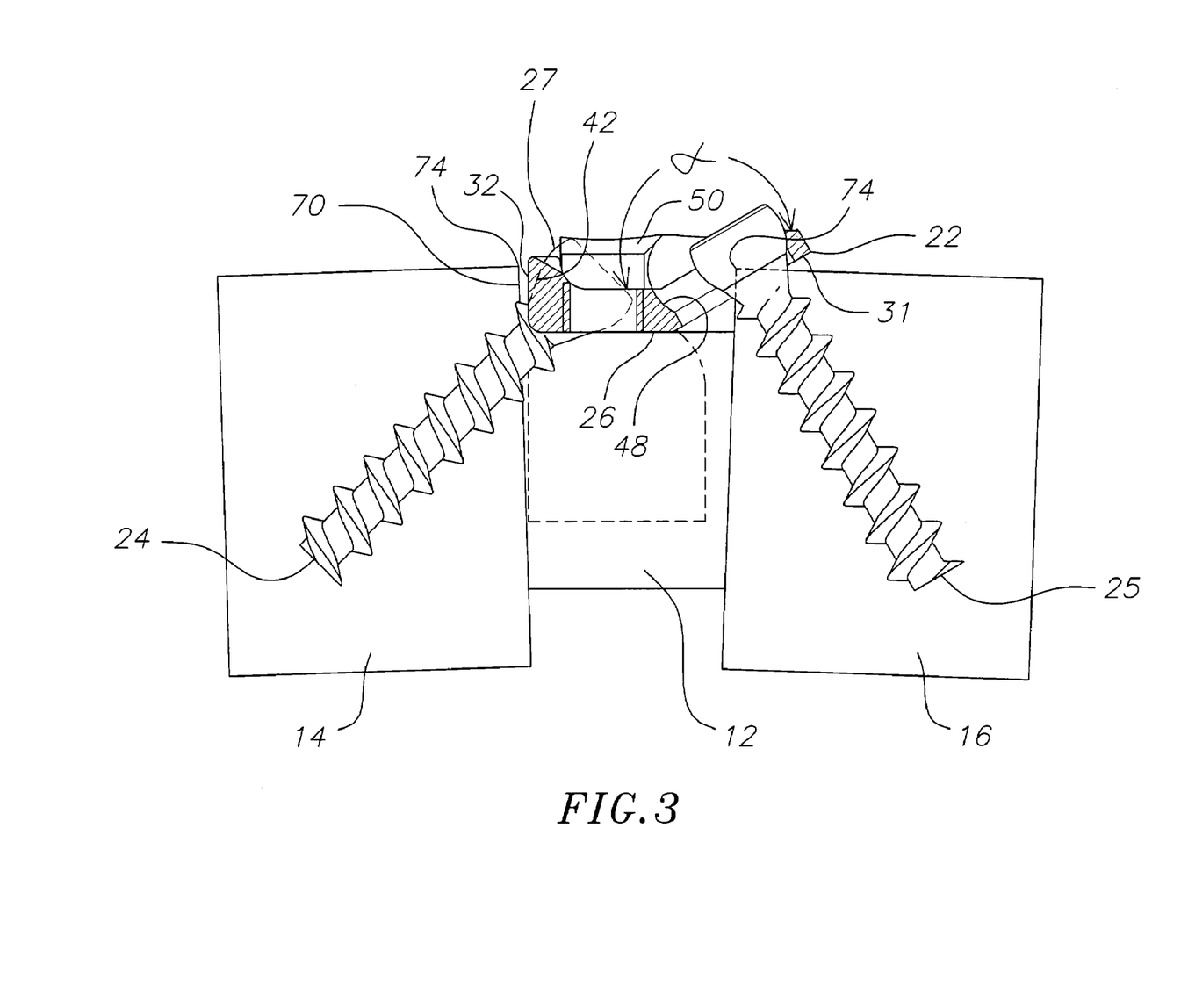
FIG. 3 is a side cross-sectional view of the bone stabilization plate system of FIG. 1 assembled between adjacent vertebrae.

FIGS. 1 and 3 show the base plate 20 mounted to first and second adjacent vertebral bodies 14 and 16 with a bone graft 12 between the vertebral bodies. The base plate 20 has a bottom surface 26 that contacts the bone graft 12. The bottom surface is therefore preferably generally flat, but can have any other design that permits it to sit against the bone graft is suitable for use in the invention. In the depicted embodiment, the bottom surface 26 of the base plate 20 is the bottom surface of the primary member 21. The primary member includes a top surface 28 that is opposite the bottom surface 26 and a side wall 32 at the first end of the base plate 20 that joins the top and bottom surfaces and contacts the first vertebral bodies 14. The top surface 28 can have any suitable design so that it can receive one or more bone screws and perform as described further below.

The secondary member 22 has a front surface 30 that is generally continuous with the top surface 28 of the primary member 21 and a back surface 31 that is generally continuous with the bottom surface 26 of the primary member. The primary member 21 and secondary member 22 are arranged relative to each other so that their top surfaces form an angle α that is greater than 90° and less than 180°, preferably from 110° to about 160°. As will become apparent, the angle at which the primary and secondary members are joined is provided so that bone screws can be introduced through the base plate at desired angles, as discussed further below. Accordingly, the base plate 20 can be designed in any other manner that permits the bone screws to be introduced therethrough at the desired angles.

Figure 4:
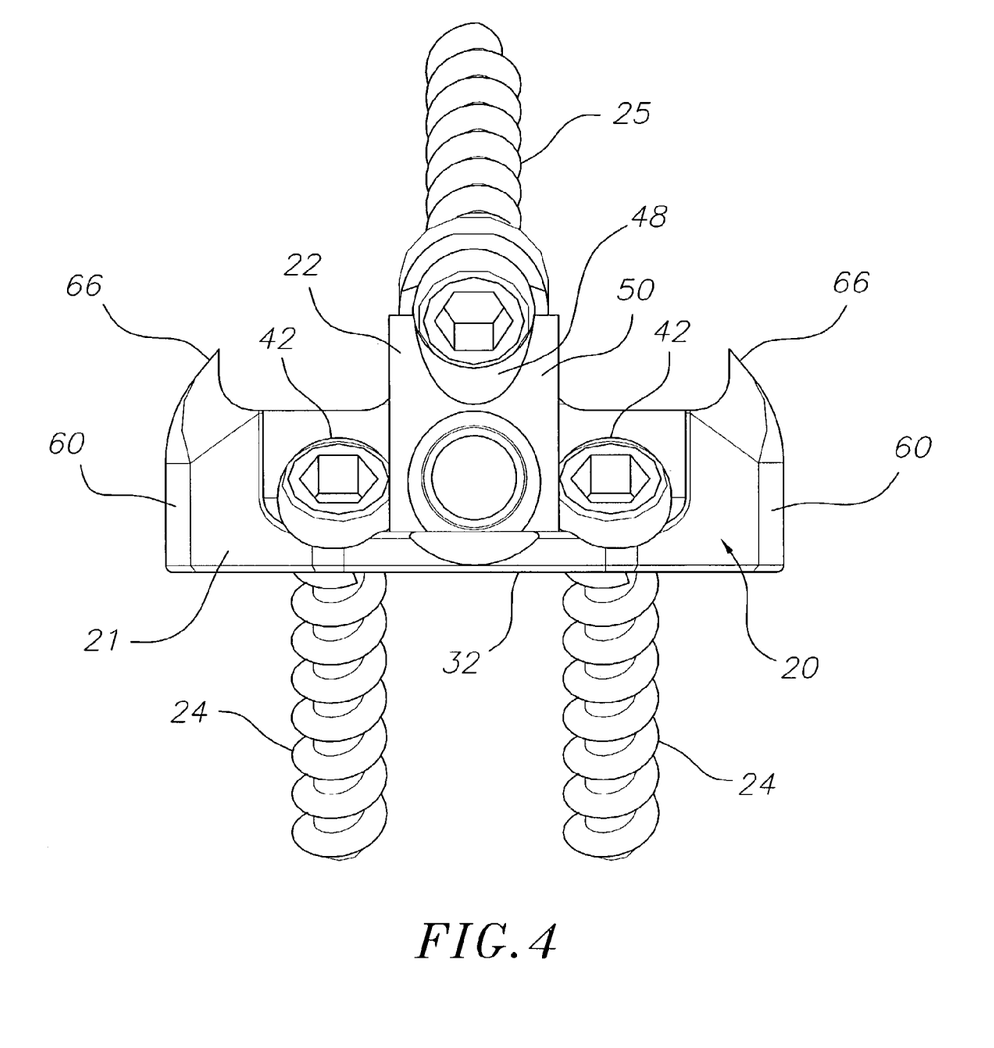
FIG. 4 is a top view of the bone stabilization plate system of FIG. 1.

The primary member 21 includes at least one, and preferably two (as shown in the depicted embodiment) first bone screw holes 42 extending therethrough for receiving a corresponding number of first bone screws 24. The bone screw holes 42 in the primary member 21 are angled relative to the bottom surface 26 of the base plate and primary member so that a first bone screw extending through first a bone screw hole extends through the base plate at an angle relative to the bottom surface, for example, through the corner joining the bottom surface 26 to the side wall 32, as best shown in FIG. 4. As a result, the each first bone screw 24 extends into the first vertebral body 14 at an angle, as discussed further below. In the depicted embodiment, each first bone screw hole 42 has a generally conical shape to receive the "radiused" shape of the bottom of the head of the corresponding first bone screw 24, described further below, but can have any other suitable shape depending upon the shape of the bone screws to be used.

The secondary member 22 includes a bone screw hole in the form of an elongated bone screw slot 48 for receiving a second bone screw 25. The second bone screw 25 is introduced into the bone screw slot 48 and into the second vertebral body 16. The bone screw slot 48 is designed so that the second bone screw 25 can slide within the slot relative to the base plate 20 generally toward the first member 21. Thus, in use, as the two vertebral bodies 14 and 16 to which the base plate 20 is fixed collapse or settle and move toward each other, the second bone screw 25 contained within the bone screw slot 48 will slide within the slot and move with the second vertebral body 16 into which it extends in a direction toward the primary member 21 and the first vertebral body 14.

Figure 5:
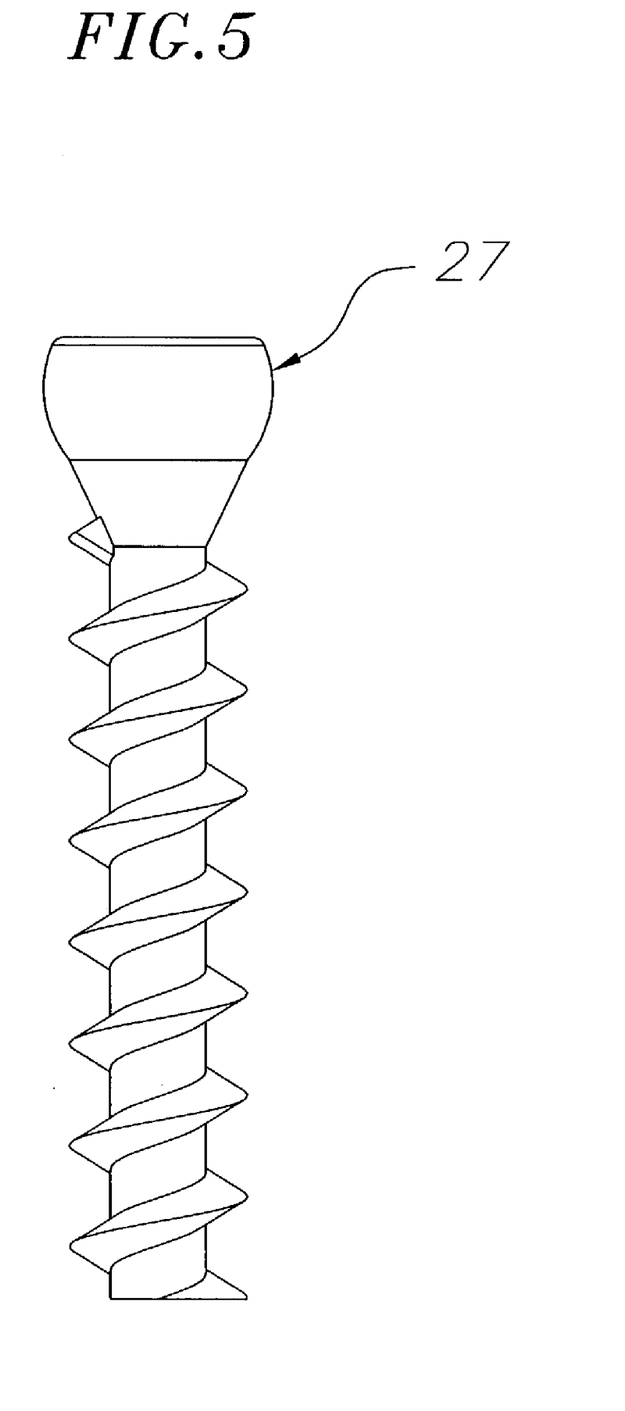
FIG. 5 is a side view of a bone screw for use in the bone stabilization plate system depicted in FIGS. 1 to 4.

The bone screws 24 and 25 can be made of any suitable material, and are preferably made of the same material as the base plate 20, such as titanium or a titanium alloy. The bone screws 24 and 25 can all have the same shape, such as that shown in FIG. 5. In the depicted embodiment, the bone screws 24 and 25 each have a radiused head 27. As used herein, the term "radiused head" means that the lower portion of the bone screw head, i.e., the portion that is nearest the shank, is generally rounded, to thereby permit the bone screws to toggle within their respective holes and slot. The bone screws 24 and 25 can have any other suitable shape that permits them to cooperate with the bone screw holes 42 and the bone screw slot 48.

The system 10 is designed so that the bone screws 24 and 25 are introduced into the vertebral bodies 14 and 15 at an angle other than 90° relative to the bone surface. Preferably the first bone screws 24 are introduced into the first vertebral body 14 so that the axis of each bone screw is at an angle relative to the bone surface ranging from about 20° to about 60°, more preferably from about 40° to about 50°. The second bone screw 25 is preferably introduced into the second vertebral body 16 so that the axis of the bone screw is at an angle relative to the bone surface ranging from about 20° to about 70°, more preferably from about 45° to about 65°.

The bone stabilization plate system includes a bone screw retaining means, which is any means for securely covering at least a part of each of the bone screws 24 and 25 so that the bone screws cannot back out from the bone once screwed in through the base plate 20. In the depicted embodiment, the bone screw retaining means comprises a retaining plate 50 and a retaining plate fixing means.

Figure 6:
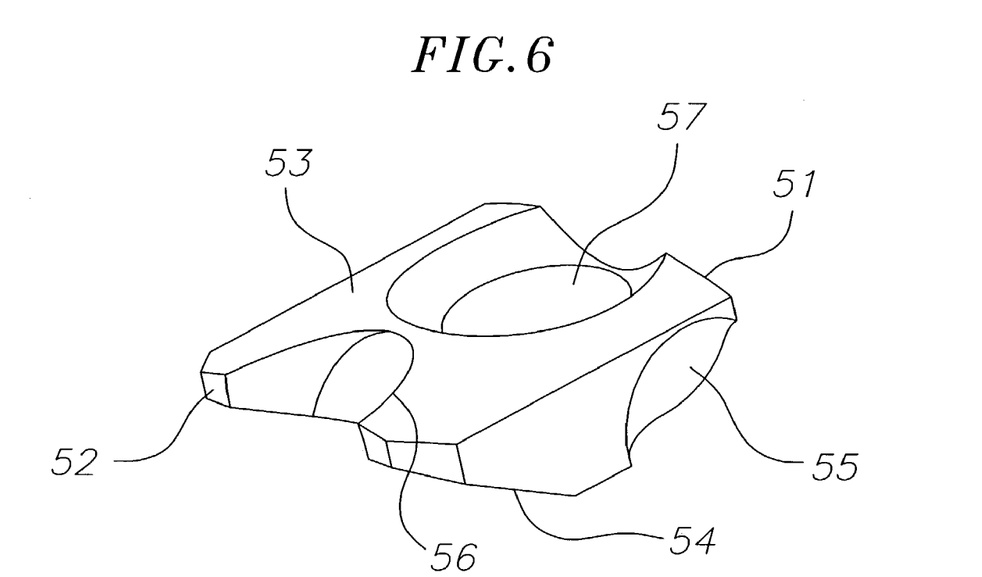
FIG. 6 is a perspective view of a retaining plate for use in the bone stabilization plate system depicted in FIGS. 1 to 4.
Figure 7:
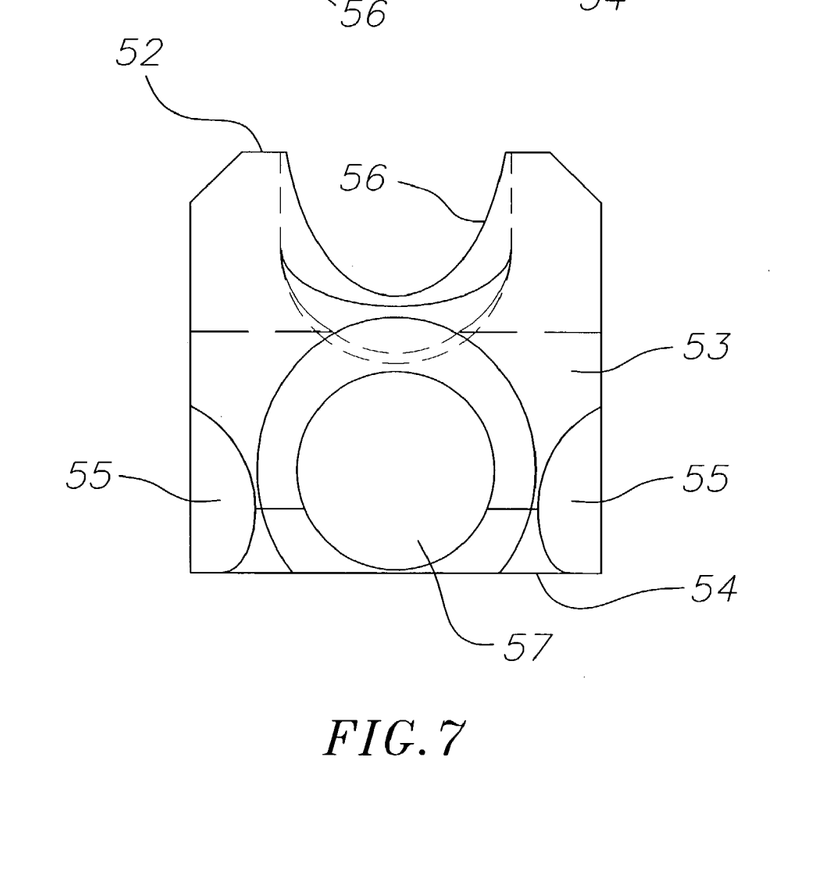
FIG. 7 is a top view of the retaining plate of FIG. 6.

As best shown in FIGS. 6 and 7, the retaining plate 50 is a generally flat plate having a first end 51, a second end 52, a top surface 53 and a bottom surface 54 that is shaped to sit against the top surface 28 of the base plate 20. In the depicted embodiment, the retaining plate 50 sits in a recessed region of the base plate 20, as best shown in FIG. 3. The use of a recessed region permits the user to more easily properly place the retaining plate on the base plate. The thickness of the retaining plate 50 is not critical, but preferably ranges from about 0.5 mm to about 2 mm, more preferably from about 1 mm to about 1.5 mm.

The retaining plate 50 includes at its first end 51 two generally-rounded notches 55 on the sides of its bottom surface 54. When the retaining plate 50 is fixed in place over the base plate 20, the two generally-rounded notches 55 each cover a portion of a corresponding one of the first bone screws 24. The generally-rounded nature of the notches 55 permits the first bone screws 24 to toggle within the first bone screw holes 42.

The retaining plate includes at its second end 52 a U-shaped notch 56, which, in the depicted embodiment, is centered at the edge of the second end. The U-shaped notch 56 includes a generally U-shaped sidewall between the top and bottom surfaces of the retaining plate that is curved outwardly from the top surface 53 to the bottom surface 54 so that the opening formed by the notch is larger at the bottom surface of the retaining plate and smaller at the top surface of the retaining plate. When the retaining plate 50 is fixed in place over the base plate 20, the top of the second bone screw 25 sits within the U-shaped notch 56 with the top of the second bone screw covered by the top surface 53 of the retaining plate. With this design, the second bone screw 25 is permitted to slide and toggle within the bone screw slot 48 even when the retaining plate 50 is fixed over the second bone screw.

The retaining plate 50 also includes a set screw aperture 57 between its first and second ends. The set screw aperture 57 in the retaining plate 50 is aligned with a set screw aperture (not shown) in the base plate 20, both of which can receive a set screw (not shown) for fixing the retaining plate in place over the base plate. The set screw can be made of any suitable material well known in the art, preferably titanium or a titanium alloy. In the preferred embodiment, the set screw is an hexagonal set screw that can be turned with an hexagonal driver. Other types of set screws can also be used, as well as any other suitable mechanism for fixing the retaining plate to the base plate. The precise mechanism by which the retaining plate is fixed to the base plate is not critical to the invention.

Any other suitable bone screw retaining means can be used in connection with the invention. For example, the bone screw retaining means can comprise multiple retaining plates that cover different bone screws. Alternatively, the bone screw retaining means can comprise one or more screws with heads that overlap at least a portion of one or more bone screws to thereby prevent the bone screws from backing out. The precise mechanism by which the bone screws are covered is not critical to the invention.

In the depicted embodiment, the base plate 20 further includes a pair of lateral tabs 60 integrally formed with the primary member 21 and extending outwardly from opposite ends of the bottom surface 26 of the primary member to form, together with the primary member, a unitary substantially U-shaped structure. In use, the lateral tabs 60 extend around the bone graft 12 to prevent lateral shift of the graft and control subsidence of adjacent vertebrae as they set during healing. The lateral tabs 60 may be made of any suitable material, and are preferably made of the same material as the base plate 20. Each tab 60 includes a generally-pointed nub 66 that extends outwardly from its corresponding tab. The function of the nubs 66 is described further below.

In use, the base plate 20 is placed directly on the bone graft 12 such that the bottom surface 26 contacts the bone graft and the side wall 32 engages a side 70 of the first vertebral body 14, as shown in FIGS. 1 and 3. The secondary member 22 engages a corner or the lip osteophite 74 of the second vertebral body 16. Two first bone screws 24 are inserted into the first bone screw holes 42 in the base plate 20 to anchor the base plate to the first vertebral body 14. The first bone screws 24 received by the first bone screw holes 42 penetrate the vertebral body 14 in an angled alignment. The axial angle of the first bone screw holes 42 determines the angle at which the first bone screws 24 will be introduced through the first vertebral body 14.

The secondary member 22 is secured to the second vertebral body 16 by the second bone screw 25 being received through the bone screw slot 48. The second bone screw 25 received by the bone screw slot 48 penetrates the second vertebral body 16 through the lip osteophite 74. It is preferred to anchor the base plate 20 to the vertebral body 16 through the lip osteophite because the lip osteophite is structurally the strongest part of the bone. The angle of the secondary member 22 relative to the primary member 21 and the angle through which the bone screw slot 48 extends through the second member determine the angle at which the second bone screw 25 will be inserted in the second vertebral body 16.

To provide an enhanced fit, a few millimeters of bone can be trimmed or otherwise removed from the lip osteophite 74 of the second vertebral body 16 at an angle corresponding to the angle of the secondary member 22. The trimmed surface provides a substantially flat surface for anchoring the second bone screw 25 into the lip osteophite 74 of the second vertebral body 16.

The angles of the bone screws 24 and 25 relative to the bone surfaces of the vertebral bodies 14 and 16 are particularly important. As note above, the lip osteophite is the strongest part of the bone, and thus angling the bone screws through the lip osteophite increases the ability of the base plate 20 to stay anchored to the vertebral bodies. Moreover, by being angled, each bone screw 24 or 25 is positioned along the angle of rotation of the corresponding vertebral body as well as the angle of settling of the vertebral body. This places each screw in a protected position against motion of the spinal column. As a result, significant sheer forces are not exerted on the screws as the vertebral bodies rotate and settle.

As is generally known in the art, a drilling tool may be used to drill holes in the bone to "tap" or prep the bone for receiving the bone screws 24 and 25. If desired before drilling, a tack tool, a tool having an elongated stem and a removable sharp tack at its distal end, may be used to create a starter hole in the bone to facilitate drilling. After drilling, a tapping tool may be used to tap the drilled holes. Following tapping, the bone screws 24 and 25 are screwed into the drilled and tapped holes through the bone screw holes 42 and the bone screw slot 48 of the base plate 20.

Once the bone screws 24 and 25 are inserted into the bone screw holes 42 and the bone screw slot 48, the retaining plate 50 is placed over the base plate and fixed in place to prevent the screws from "backing out" of the screw holes. The second bone screw 25 that extends through the bone screw slot 48 is nonetheless permitted to slide along the length of the slot, even when the retaining plate 50 is secured in place. Thus, second the bone screw 25 and the bone screw slot 48 cooperate to control any lateral or rotary movement of one vertebral body relative to an adjacent vertebral body during "settling" of the bone. Further, the angled orientation of the second member 22 provides the base plate 20 with resilient properties, for example, enabling the base plate "flex" when one vertebrae is rotated relative to an adjacent vertebrae.

As noted above, all of the bone screws 24 and 25 are preferably permitted to toggle, or pivot, even after the retaining plate 50 is fixed over the base plate 50. The ability of the screws to toggle permits the system 10 to migrate and self-center after it has been implanted.

If the base plate 20 includes lateral tabs 60 with nubs 66, the nubs will also share in the weight-bearing during settling of the vertebral bodies. Specifically, as the vertebral bodies move toward each other during settling, the pointed nubs 66 will contact and slowly enter the second vertebral body 16 to a limited extent. This contact can help in controlling the rate of settling.

In the alternative, relatively smaller (shorter and/or smaller in diameter) bone screws may be used. Because the bone screws penetrate the lip osteophite, which is structurally the strongest portion of the bone, shorter bone screws may be used to anchor the base plate to the bone. Moreover, because the screws are positioned along the angle of rotation of the corresponding vertebral body as well as the angle of settling of the vertebral body, as discussed above, significant sheer forces are not exerted on the screws as the vertebral bodies rotate and settle, thereby minimizing the diameter of screw needed.

The present invention provides an additional benefit of providing a vertebral support device having a "low profile." Namely, the base plate of the present invention is specially designed to have an outer periphery that coincides with or generally matches the outer diameter of the cortex. The top surface of the base sits at, and preferably below, the top surface of the vertebral bodies. As such, the bone plate system of the present invention does not have any parts that would significantly interfere with or irritate the trachea, esophagus, and/or other sensory nerves of the user.

Another advantage of the present bone plate system is that it is stackable. Frequently after a bone graft is inserted and a bone plate joined to the surrounding vertebral bodies, for example, C4 and C5, an adjacent disk, for example, between C5 and C6, subsequently deteriorates. With traditional bone plates, it would be necessary to remove the plate from C5 before attaching a second bone plate to C5 and C6 because each plate covers a significant surface of the vertebral body. To remove a bone plate, it is necessary cut through scar tissue, which can have a negative impact on the patient. In contrast, the bone plate systems of the present invention cover an insignificant portion of the top surfaces of the vertebral bodies to which it is attached, instead being located primarily between the vertebral bodies. As a result, multiple bone plate systems can be introduced over adjacent bone grafts (i.e., between a common vertebral body) so that two bone plate systems are attached to a common vertebral body without the bone plate systems contacting one another. Thus, subsequent procedures where new bone grafts are to be inserted do not require the removal of a pre-existing bone plate prior to introduction of a new bone plate. The depicted systems where the bone screws are provided in a generally triangular arrangement further enhances the stacking ability of the bone plate systems of the invention.

It is presently preferred to provide a kit having base plates of different sizes, bone screws of differing lengths and retaining plates complementary to the base plates. The kit may further comprise a tack tool, a drilling tool, tapping tool and/or one or more screw driving tools.

While preferred embodiments of the present invention are described for supporting adjacent cervical vertebrae in the anterior region of the vertebrae, persons skilled in the art would recognize that the bone pate of the present invention may be utilized to support adjoining thoracic and lumbar vertebrae in the lateral or posterior regions of the vertebrae. Further, the device and method of the invention is not limited to vertebral bodies, but can also be use to join two other pieces of bone in other parts of the body.

While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A method for joining first and second bones having top surfaces and side surfaces generally facing each other, the method comprising:

inserting between the side surfaces of the bones a base plate having a first end nearer the first bone and a second end nearer the second bone, wherein the base plate has a first screw hole extending through the first end and a second screw hole extending through the second end;

introducing a first bone screw through the first screw hole and into the first bone, wherein the first bone screw is introduced at an angle relative to the top surface of the bone ranging from about 20° to about 60°, introducing a second bone screw through the second screw hole and into the second bone, wherein the second bone screw is introduced at an angle relative to the top surface of the bone ranging from about 20° to about 70°, and covering at least a part of the first bone screw and at least a part of the second bone screw to prevent the first and second bone screws from backing out of the first and second bones, respectively.

2. The method according to claim 1, wherein the first bone screw is introduced into the first bone at a corner of the bone formed between the top surface and side surface of the first bone.

3. The method according to claim 2, wherein the second bone screw is introduced into the second bone at a corner of the bone formed between the top surface and side surface of the second bone.

4. The method according to claim 1, wherein the second bone screw is introduced into the second bone at a corner of the bone formed between the top surface and side surface of the second bone.

5. The method according to claim 4, wherein the base plate has a top surface that sits at or below the top surfaces of the first and second bones.

6. The method according to claim 1, wherein the first and second bones are first and second vertebral bodies, respectively, and wherein the first bone screw is introduced into the lip osteophite of the first vertebral body and the second bone screw is introduced into the lip osteophite of the second vertebral body.

7. The method according to claim 6, wherein the base plate has a top surface that sits at or below the top surfaces of the first and second vertebral bodies.

8. The method according to claim 1, wherein the base plate has a top surface that sits at or below the top surfaces of the first and second bones.

9. The method according to claim 1, wherein the first bone screw is introduced at an angle relative to the top surface of the bone ranging from about 40° to about 50°.

10. The method according to claim 1, wherein the second bone screw is introduced at an angle relative to the top surface of the bone ranging from about 45° to about 65°.

11. The method according to claim 1, wherein the second bone screw hole comprises an elongated slot in which the second bone screw can slide relative to the base plate.

12. The method according to claim 1, wherein, when the first and second bone screws are covered, they are permitted to toggle relative to the base plate.

13. The method according to claim 1, wherein the first and second bone screws are covered by a single retaining plate.

14. The method according to claim 1, wherein the base plate has a third screw hole extending through the first end, the method further comprising:

introducing a third bone screw through the third screw hole and into the first bone, wherein the third bone screw is introduced at an angle relative to the top surface of the bone ranging from about 20° to about 60°, and covering at least a part of the third bone screw to prevent the third bone screw from backing out of the first bone.

15. The method according to claim 14, wherein:

the first bone screw is introduced into the first bone at a corner of the bone formed between the top surface and side surface of the first bone;

the second bone screw is introduced into the second bone at a corner of the bone formed between the top surface end side surface of the second bone; and the third bone screw is introduced into the first bone at a corner of the bone formed between the top surface and side surface of the second bone.

16. The method according to claim 14, wherein the first and second bones are first and second vertebral bodies, respectively, and wherein the first and third bone screws are introduced into the lip osteophite of the first vertebral body, and the second bone screw is introduced into the lip osteophite of the second vertebral body.

17. The method according to claim 14, wherein, when the first, second and third bone screws are covered, they are permitted to toggle relative to the base plate.

18. The method according to claim 14, wherein the first, second and third bone screws are covered by a single retaining plate.

19. The method according to claim 1, wherein the first and second bones are first and second vertebral bodies, the method further comprising introducing a bone graft between the side surfaces of the first and second vertebral bodies prior to insertion of the base plate.

20. The method according to claim 19, wherein the base plate includes a first member that sits on a top surface of the bone graft and first and second tabs extending from the first member along first and second side surfaces of the bone graft in a direction generally transverse to the first and second vertebral bodies.

21. The method according to claim 20, wherein the first and second tabs each include a generally-pointed nub that contacts the side surface of the first vertebral body.

22. A bone stabilization plate system comprising:

a base plate having bottom surface and first and second ends, the first end comprising a first bone screw region having a first bone screw hole extending therethrough at an angle relative to the bottom surface of the base plate ranging from about 20° to about 60°, and the second end comprising a second bone screw region having a second bone screw hole extending therethrough at an angle relative to the bottom surface of the base plate ranging from about 20° to about 70°;

a first bone screw capable of securing the base plate to a first bone by insertion through the first bone screw hole;

a second bone screw capable of securing the base plate to a second bone by insertion through the second bone screw hole; and a bone screw retaining means for securedly covering at least a part of the first and second bone screws to prevent the bone screws from backing out from the first and second bones.

23. The bone stabilization plate system according to claim 22, wherein the base plate comprises a primary member having a generally flat bottom surface and a secondary member adjacent the primary member, the secondary member having a bottom surface that is generally transverse to the bottom surface of the primary member, and where the first bone screw hole extends through the primary member and the second bone screw hole extends through the secondary member.

24. The bone stabilization plate system according to claim 22, wherein the first bone screw hole extends through the base plate at an angle relative to the bottom surface of the base plate ranging from about 40° to about 50°.

25. The bone stabilization plate system according to claim 22, wherein the second bone screw hole extends through the base plate at an angle relative to the bottom surface of the base plate ranging from about 45° to about 65°.

26. The bone stabilization plate system according to claim 22, wherein the second bone screw hole comprises an elongated slot in which the second bone screw can slide relative to the base plate.

27. The bone stabilization plate system according to claim 22, wherein, when the first and second bone screws are covered by the bone screw retaining means, they are permitted to toggle relative to the base plate.

28. The bone stabilization plate system according to claim 22, wherein the first and second bone screws are covered by a single retaining plate.

29. The bone stabilization plate system according to claim 22, wherein the base plate has a third screw hole extending through the first end of the base plate at an angle relative to the bottom surface of the base plate ranging from about 20° to about 60°, and where the system further comprises a third bone screw capable of securing the base plate to the first bone by insertion through the third bone screw hole.

30. The bone stabilization plate system according to claim 29, wherein, when the first, second and third bone screws are covered by the bone screw retaining means, they are permitted to toggle relative to the base plate.

31. The bone stabilization plate system according to claim 29, wherein the first, second and third bone screws are covered by a single retaining plate.

32. The bone stabilization plate system according to claim 22, wherein the base plate includes a first member that sits on a top surface of a bone graft and first and second tabs extending from the first member along first and second side surfaces of the bone graft in a direction generally transverse to first and second vertebral bodies.

33. The bone stabilization plate system according to claim 32, wherein the first and second tabs each include a generally-pointed nub.

34. A method for joining vertebral bodies, comprising:
inserting between side surfaces of first and second adjacent vertebral body a first base plate having a first end nearer the first vertebral body and a second end nearer the second vertebral body, wherein the first base plate has a first screw hole extending through the first end and a second screw hole extending through the second end;
introducing a first bone screw through the first screw hole and into the first bone;
introducing a second bone screw through the second screw hole and into the second bone;
covering at least a part of the first bone screw and at least a part of the second bone screw to prevent the first and second bone screws from backing out of the first and second bones, respectively;
inserting between a side surface of the second vertebral body and a side surface of a third vertebral body that is adjacent the second vertebral body a second base plate having a first end nearer the second vertebral body and a second end nearer the third vertebral body, wherein the second base plate has a first screw hole extending through its first end and a second screw hole extending through its second end;
introducing a third bone screw through the first screw hole of the second base plate and into the second bone;
introducing a fourth bone screw through the second screw hole of the second base plate and into the third bone; and
covering at least a part of the third bone screw and at least a part of the fourth bone screw to prevent the third and fourth bone screws from backing out of the second and third bones, respectively;
wherein the first base plate does not contact the second base plate.

35. A bone stabilization plate system including a base plate for retaining bone graft material between first and second longitudinally-aligned, adjacent bone bodies and for permitting force transmission between the first and second bone bodies through the bone graft material, the base plate being sized to have an inter-fit between the first and second adjacent bone bodies and adjacent to lateral extents of the bone graft material such that the first and second bone bodies engage the bone graft material, and at least first and second bone screws for extending into the first and second bone bodies, respectively, to retain the base plate between the first and second bone bodies, the base plate having means for interacting with the first and second bone screws, the means for interacting including means for permitting movement of at least one of the first and second bone bodies relative to the base plate.

36. The bone stabilization plate system according to claim 35, wherein at least one of the bone screws includes an arcuate surface and the means for interacting includes a surface that engages the arcuate surface of the at least one bone screw and permits relative movement between the bone screw and the base plate.

37. The bone stabilization plate system according to claim 35, wherein the base plate includes two lateral tabs for location between the first and second adjacent bone bodies, the lateral tabs are spaced apart from each other such that ends of the lateral tabs provide for an open space of the base plate for location of the bone graft material therein.

38. The bone stabilization plate system according to claim 37, wherein the two lateral tabs include at least one portion shaped to penetrate into at least one of the first and second adjacent bone bodies.

39. The bone stabilization plate system according to claim 35, wherein each of the bone bodies has an outwardly-facing surface and each of the bone bodies has a side surface facing toward the side surface of the other bone body, the base plate having a first end portion adjacent to the first bone body, the first end portion having an outwardly-facing surface for location at a position recessed relative to the outwardly-facing surface of the first bone body, the first end portion having a first screw hole that opens toward the side surface of the first bone body, the base plate having a second end portion that has a second screw hole that opens toward the second bone body, the first and second bone screws extending through the first and second holes into the first and second bone bodies, respectively, each at an angle that is non-orthogonal to the longitudinal alignment of the first and second bone bodies.

40. A bone stabilization plate system including a U-shaped base plate for positioning onto bone graft material placed at a location between first and second longitudinally-aligned, adjacent bone bodies and for retaining the bone graft material at the location between the first and second bone bodies, the base plate being sized to have an inter-fit between the first and second adjacent bone bodies and adjacent to lateral extents of the bone graft material, wherein each of the bone bodies has an outwardly-facing surface and each of the bone bodies has a side surface facing toward the side surface of the other bone body, the base plate having a first end portion adjacent to the first bone body, the first end portion having an outwardly-facing surface for location at a position recessed relative to the outwardly-facing surface of the first bone body, the first end portion having a first screw hole that opens toward the side surface of the first bone body, the base plate having a second end portion that has a second screw hole that opens toward the second bone body, and at least first and second bone screws for extending through the first and second holes into the first and second bone bodies, respectively, each at an angle that is non-orthogonal to the longitudinal alignment of the first and second bone bodies.

41. A method for stabilizing first and second longitudinally-aligned, adjacent bone bodies and for retaining a bone graft material at the location between the first and second bone bodies, wherein each of the bone bodies has an outwardly-facing surface and each of the bone bodies has a side surface facing toward the side surface of the other bone body, the method including positioning a U-shaped base plate onto the bone graft material, with the base plate being sized to have an inter-fit between the first and second adjacent bone bodies and adjacent to lateral extents of the bone graft material, with a first end portion of the base plate being adjacent to the first bone body and having an outwardly-facing surface of the first end portion located at a position recessed relative to the outwardly-facing surface of the first bone body, extending a first bone screw through a first screw hole at the first end portion and into the side surface of the first bone body at an angle that is non-orthogonal to the longitudinal alignment of the first and second bone bodies, and extending a second bone screw through a second screw hole at a second end portion of the base plate and into the second bone body at an angle that is non-orthogonal to the longitudinal alignment of the first and second bone bodies.

* * * * *

UNITED STATES PATENT AND TRADEMARK OFFICE
CERTIFICATE OF CORRECTION

| | |
|---|---|
| PATENT NO. | : 6,984,234 B2 |
| DATED | : January 10, 2006 |
| INVENTOR(S) | : Robert S. Bray |

It is certified that error appears in the above-identified patent and that said Letters Patent is hereby corrected as shown below:

<u>Column 10,</u>
Line 7, delete "end" and insert -- and --.

Signed and Sealed this

Seventh Day of March, 2006

JON W. DUDAS
*Director of the United States Patent and Trademark Office*